(12) United States Patent
Omote et al.

(10) Patent No.: US 8,699,663 B2
(45) Date of Patent: Apr. 15, 2014

(54) X-RAY IMAGE PHOTOGRAPHING METHOD AND X-RAY IMAGE PHOTOGRAPHING APPARATUS

(75) Inventors: Kazuhiko Omote, Akiruno (JP); Makoto Kambe, Fussa (JP); Yoshihiro Takeda, Ome (JP)

(73) Assignee: Rigaku Corporation, Tokyo (JP)

( * ) Notice: Subject to any disclaimer, the term of this patent is extended or adjusted under 35 U.S.C. 154(b) by 309 days.

(21) Appl. No.: 13/233,739

(22) Filed: Sep. 15, 2011

(65) Prior Publication Data

US 2012/0087470 A1      Apr. 12, 2012

(30) Foreign Application Priority Data

Oct. 7, 2010   (JP) ................................. 2010-227872

(51) Int. Cl.
    *G01N 23/20*      (2006.01)
(52) U.S. Cl.
    USPC .............................................. 378/62; 378/51
(58) Field of Classification Search
    USPC .................................................... 378/62, 51
    See application file for complete search history.

(56) References Cited

U.S. PATENT DOCUMENTS

| 7,400,704 | B1 | 7/2008 | Yun et al. |
| 7,746,977 | B2 | 6/2010 | Shinden et al. |
| 2005/0147205 | A1* | 7/2005 | Dolazza et al. ................. 378/37 |
| 2009/0116615 | A1 | 5/2009 | Shinden et al. |

FOREIGN PATENT DOCUMENTS

| JP | 2001-238871 A | 9/2001 |
| JP | 2006-26425 A | 2/2006 |
| JP | WO 2007/007473 A1 | 1/2007 |

OTHER PUBLICATIONS

Ohara et al., "The Principle and Images of Phase-Contrast Mammography," 2006, vol. 23, No. 2, p. 27-33.

* cited by examiner

*Primary Examiner* — Hoon Song
(74) *Attorney, Agent, or Firm* — Birch, Stewart, Kolasch & Birch, LLP

(57) ABSTRACT

There is provided an X-ray image photographing method and an X-ray image photographing apparatus capable of photographing a high resolution phase contrast image and a high resolution absorption contrast image in a short time according to the purpose only by finely adjusting the distance between a specimen and a detector with respect to an X-ray source. The X-ray image photographing method enables photographing of a fine structure with a high space resolution while d/L is sufficiently smaller than 1, when L is a distance from an X-ray source 110 to a specimen 500 and d is a distance from the specimen 500 to a detector 130. Further, a distance between a peak position and a valley position of a phase contrast is not less than $\frac{1}{3}\Delta$ and not more than $3\Delta$, when $\lambda$ is an average wavelength of the X-ray and $\Delta$ is a resolution of the detector 130.

7 Claims, 15 Drawing Sheets

X-RAY IMAGE PHOTOGRAPHING METHOD AND X-RAY IMAGE PHOTOGRAPHING APPARATUS

BACKGROUND OF THE INVENTION

1. Field of the Invention

The present invention relates to an X-ray image photographing method and an X-ray image photographing apparatus which enables photographing of a fine structure while using an X-ray source having a finite size.

2. Description of the Related Art

Conventionally, in a field of X-ray transmission image photographing, resolution of a detector has been at most ten and several μm. Accordingly, in order to photograph an image having a high resolution, photographing has been performed by magnifying projection of a specimen by using an X-ray source having a focal point size as small as possible, about 10 μm or less. That is, magnification ratio has been adjusted by adjusting distance relationships by reducing the distance from the X-ray source to the specimen and setting the distance from the specimen to the detector sufficiently large.

On the other hand, a method for performing photographing using a phase contrast and photographing using an absorption contrast with a same apparatus has been investigated (JP 2001-238871 A, JP 2006-26425 A, WO 2007/007473A, Hiromu OHARA, Tomonori GIDO, Akira ISHISAKA, and Chika HONDA, "The Principle and Images of Phase-Contrast Mammography", Vol. 23 (2006), No. 2, pp. 27-33). For example, JP 2001-238871 A discloses a photographing method of an image with an emphasized edge by utilizing a phase contrast, with the ratio of the distance from the specimen to the detector and the distance from the X-ray source to the specimen set to 0.5.

However, in the photographing method of an X-ray transmission image using the above-mentioned magnified projection, the magnification ratio is determined by the arrangement of the X-ray source, the specimen, and the detector. Accordingly, under high magnification ratio photographing conditions for photographing a fine structure with a high resolution, it is not easy to freely adjust the ratio of phase contrast and absorption contrast while keeping the magnification ratio. On the other hand, in a method using electron beam such as SEM or TEM, it is difficult to photograph the structure inside a thick specimen although it is possible to obtain an image having a high resolution with respect to a specimen surface or a thin specimen.

SUMMARY OF THE INVENTION

The present invention is made in light of such circumstances. It is an object of the present invention to provide an X-ray image photographing method and an X-ray image photographing apparatus capable of photographing a high resolution phase contrast image and a high resolution absorption contrast image in a short time according to the purpose only by finely adjusting the distance between a specimen and a detector with respect to an X-ray source.

(1) In order to achieve the above object, the X-ray image photographing method according to the invention is an X-ray image photographing method that enables photographing of a fine structure with a high space resolution while using an X-ray source having a finite size, wherein:

d/L is sufficiently smaller than 1, when L is a distance from an X-ray source to a specimen and d is a distance from the specimen to a detector; and the following formula is satisfied:

$$\frac{\Delta}{3} \leq 0.96\sqrt{\lambda \cdot d} \leq 3\Delta$$

wherein λ is a wavelength of X-ray to be irradiated from the X-ray source and Δ is a resolution of the detector.

In a normal X-ray source, X-ray to be irradiated includes not only a single wavelength λ, but also a number of X-ray wavelengths. In such a case, λ of the formula 1 is substituted to a weighted average numerical number in accordance with a spectrum to be irradiated to the specimen.

With the above-mentioned characteristics, it becomes possible to photograph a phase contrast image in which the outline of the specimen is emphasized in a micron order, and to perform CT reconstruction by an absorption contrast, only by adjusting arrangements of a specimen and a detector with respect to an X-ray source within a range of d/L<<1. Furthermore, it becomes possible to use a high-output X-ray source having a relatively large focal point size and to obtain an X-ray transmission image having a high resolution in a short time. That sufficiently smaller than 1 means that photographing magnification ratio described by (L+d)/L=1+d/L can be nearly approximated by one.

(2) In the X-ray image photographing method according to the invention, the d/L is 0.1 or less. Accordingly, not only an image having a resolution of not more than a several micron can be obtained by using a detector with a high resolution even when a high-output X-ray source having a sufficiently large focal point size, but also a stable photographing can be performed with respect to a drift of a focal position of the X-ray source.

(3) In the X-ray image photographing method according to the invention, a focal point size of the X-ray source is sufficiently larger than the Δ. Accordingly, an X-ray source of a high output can be used without being limited by the focal point size. That sufficiently large means the level that satisfies, for example, S>10Δ.

(4) In the X-ray image photographing method according to the invention, the detector has a space resolution of 2 μm or less. Accordingly, an X-ray transmission image can be detected with a high resolution.

(5) In the X-ray image photographing method according to the invention, supply power when the X-ray source is used is 30 W or more. Accordingly, photographing can be performed in a short time by using a large power.

(6) In the X-ray image photographing method according to the invention, a fine focal point formed by focusing divergent X-ray with an X-ray optical element is used as a virtual source for the X-ray source. Accordingly, photographing can be performed by a single λ when a monochromatic virtual source is used. Furthermore, absorption coefficient can be also quantitatively calculated, and it becomes possible to perform CT reconstruction having quantitative density information.

(7) Furthermore, an X-ray image photographing apparatus according to the invention includes: an X-ray source having a finite size and generating X-ray; a support table supporting a specimen to which the generated X-ray is irradiated; and a detector detecting X-ray transmitted through the specimen, wherein d/L is set to be sufficiently smaller than 1 by adjusting an arrangement of the X-ray source, the support table, and the detector to thereby enable photographing of a fine structure of the specimen, wherein L is a distance from the X-ray source to the specimen and d is a distance from the specimen to the detector.

Accordingly, it becomes possible to photograph an image by a phase contrast in which the outline of the specimen is emphasized by adjusting the arrangement of the specimen and the detector with respect to the X-ray source, to selectively photograph an image of an absorption contrast freely, and to perform CT reconstruction in which quantitative performance is high and artifact is small. Furthermore, by using a high-powered X-ray source, an X-ray transmission image having a high resolution can be obtained in a short time.

According to the invention, by performing fine adjustment of the arrangement of the specimen and the detector with respective to the X-ray source, a phase contrast image and an absorption contrast image can be photographed in a short time and with a high resolution.

DETAILED DESCRIPTION OF THE INVENTION

Figure 1:
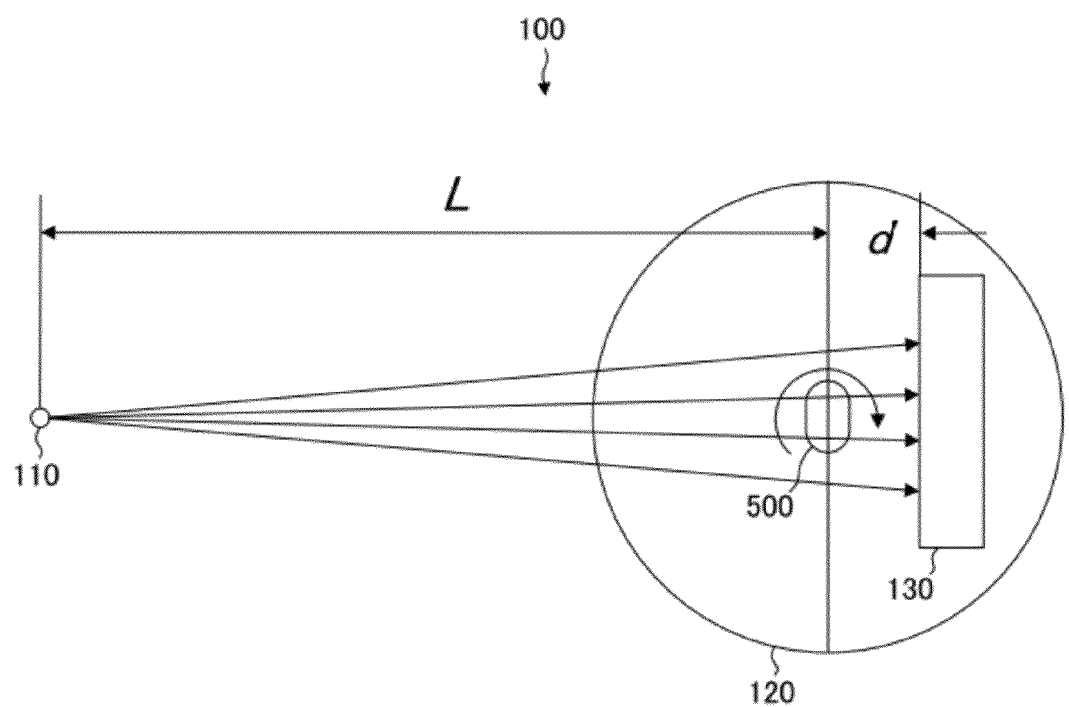
FIG. 1 is a schematic diagram showing a configuration for an X-ray image photographing method according to the invention.

Best Modes for Carrying Out the Invention

Next, embodiments of the invention are described with reference to the accompanying drawings. For easy understanding of the description, the same reference numerals are used to designate the same components in each drawing, and duplicated description will be omitted.

First Embodiment

Apparatus Configuration

FIG. 1 is a schematic diagram showing a configuration for an X-ray image photographing method of the invention. Such a configuration is configured by arrangement of each unit of an X-ray image photographing apparatus 100. As shown in FIG. 1, the X-ray image photographing apparatus 100 includes an X-ray source 110, a support table 120, and a detector 130.

The X-ray source 110 is an X-ray source having a finite focal point size and used in a laboratory. Radiation light by synchrotron radiation is not used in the X-ray source 110. To be more specific, copper, molybdenum, tungsten, etc., is used as an X-ray source target, and the arrangement of each unit is adjusted in accordance with the wavelength of characteristic X-ray, the type of which is not particularly limited. The X-ray source 110 is not necessarily limited to electronic collision type, plasma X-ray, inverse Compton radiation, etc., and a virtual source to be described below is also included.

It is preferable that the focal point size of the X-ray source 110 be sufficiently larger than resolution $\Delta$ of the detector. Accordingly, the X-ray source 110 having a high output can be used without being limited by the focal point size. Since d/L is sufficiently smaller than 1, stable photographing can be performed with respect to a drift of a focal position of the X-ray source 110. It is preferable that supply power to the X-ray source 110 be 30 W or more, and more preferably, 100 W or more. In this manner, by supplying large power, an X-ray image can be photographed in a short time.

The support table 120 supports a specimen 500 to which X-ray is irradiated. The support table 120 is capable of fixing the specimen 500, and capable of rotation control. It is preferable that run-out of the rotation axis be small, and in particular, the swing be 1 μm or less. Accordingly, CT reconstruction having a high resolution can be realized without being corrected by software.

The detector 130 detects X-ray transmitted through the specimen 500. The detector 130 has a high spatial resolution of less than 10 μm. It is preferable that the spatial resolution of the detector 130 be 7 μm or less, and more preferably, 1 μm or less. Accordingly, detection with a high resolution becomes possible by utilizing an X-ray transmission image having a high resolution. In the X-ray image photographing apparatus 100 in case of using monochromatic X-ray by using a virtual source, an image having a high contrast can be obtained also to a fine specimen, and the X-ray image photographing apparatus 100 is suitable for observing a fine structure such as soft structure of living organism and an industrial product of an organic substance.

Furthermore, the X-ray image photographing apparatus 100 has, for example, a slide mechanism (not shown) and capable of fine adjustment by controlling the arrangement of the support table 120 or the detector 130 with respect to the X-ray source 110. An image with outline emphasized by a phase contrast or an image suitable for CT reconstruction by an absorption contrast can be photographed by fine adjustment within the range of d/L<<1. In this adjustment, since d/Δ<<1, magnification ratio (L+D)/L=1+d/L is about one, so that it also becomes possible to adjust the level of phase contrast without changing magnification ratio and viewing field.

(Photographing)

An image can be photographed by using the X-ray image photographing apparatus 100 configured as described above. When the distance from the X-ray source 110 to the specimen 500 is denoted by L, and the distance from the specimen 500 to the detector 130 is denoted by d, the arrangement of the X-ray source 110, the support table 120, and the detector 130 is adjusted and measured with d/L reduced to be sufficiently smaller than 1. It is preferable that d/L be 0.1 or less. This makes it possible to photograph the fine structure of the specimen 500.

Figure 2:
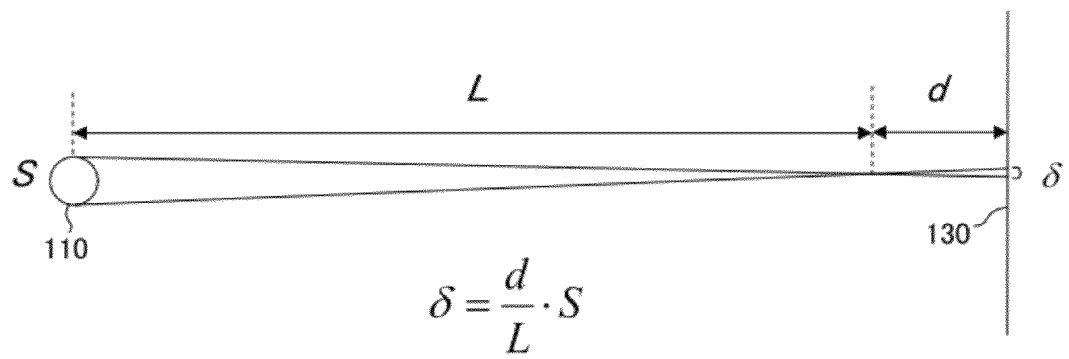
FIG. 2 is a diagram showing a relationship between a focal point and a projection.

FIG. 2 is a diagram showing a relationship between a focal point and a projection. In the above-mentioned arrangement, since d/L is small and a focal point size S of the X-ray source is reduced to be projected by d/L times on the detector 130, an image of the X-ray source to be projected on the detector 130 is reduced by d/L times. Accordingly, not only an image having a high resolution can be photographed even when an X-ray source of sufficiently large focal point size is used, but also influence of drift of the focal position can be restrained to a small level. In this manner, as a result of being capable of using a high output X-ray source having a large focal point size, efficient photographing in a short time becomes possible.

The arrangement of each unit of the X-ray image photographing apparatus 100 also satisfies the following condition besides sufficiently reducing d/L. That is, when an average wavelength of the X-ray to be irradiated from the X-ray source 110 is denoted by $\lambda$, and the resolution of the detector 130 is denoted by $\Delta$, the configuration of the X-ray image photographing apparatus 100 satisfies the following formula.

$$\frac{\Delta}{3} \le 0.96\sqrt{\lambda \cdot d} \le 3\Delta \quad (1)$$

By adjusting the distance d from the specimen 500 to the detector 130 within the range of the formula (1), it becomes possible to photograph an image in which the outline of the specimen is emphasized by a phase contrast by adjusting the arrangement of the specimen 500 and the detector 130 with respect to the X-ray source 110, and to photograph an image for CT reconstruction by an absorption contrast.

Figure 3:
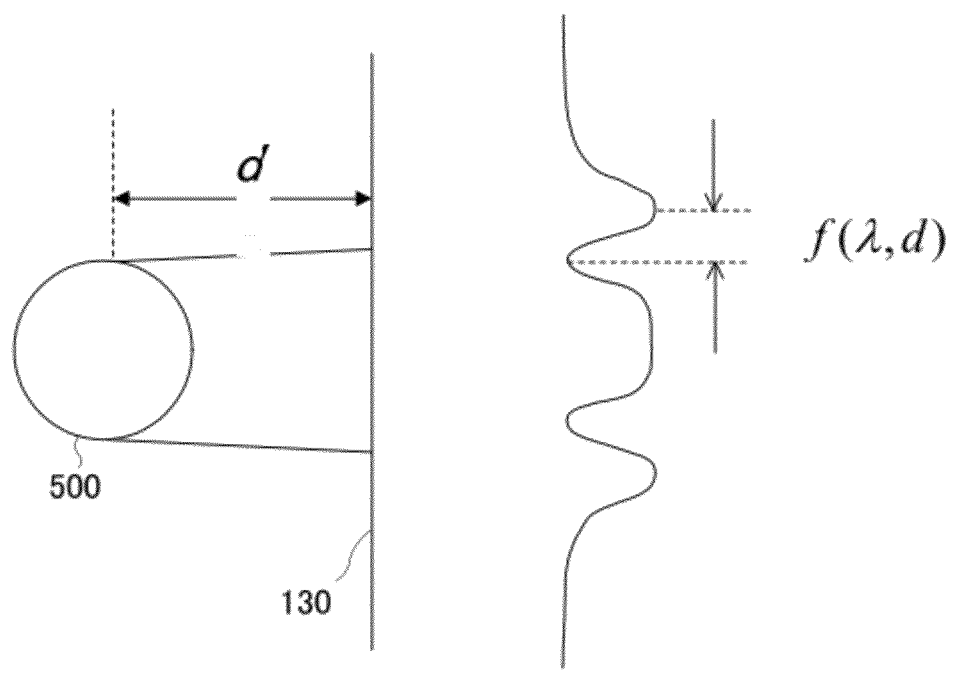
FIG. 3 is a diagram showing a distance between a peak position and a valley position of a phase contrast.

X-ray is diffusely projected by refraction and a shadow is projected. Distribution profile of the projected intensity is determined by the distance d between the position of the specimen 500 and the detector 130. The X-ray image photographing apparatus 100 is capable of adjusting the distance d to a preferred length. FIG. 3 is a diagram showing the distance between a peak position and a valley position of a phase contrast. The distance $f(\lambda, d)$ between the peak position and the valley position of the phase contrast is so called a phase contrast (fringe of phase) and can be obtained as described below by considering Fresnel diffraction.

$$f(\lambda, d) = 0.96\sqrt{\lambda \cdot d} \quad (2)$$

Figure 4:
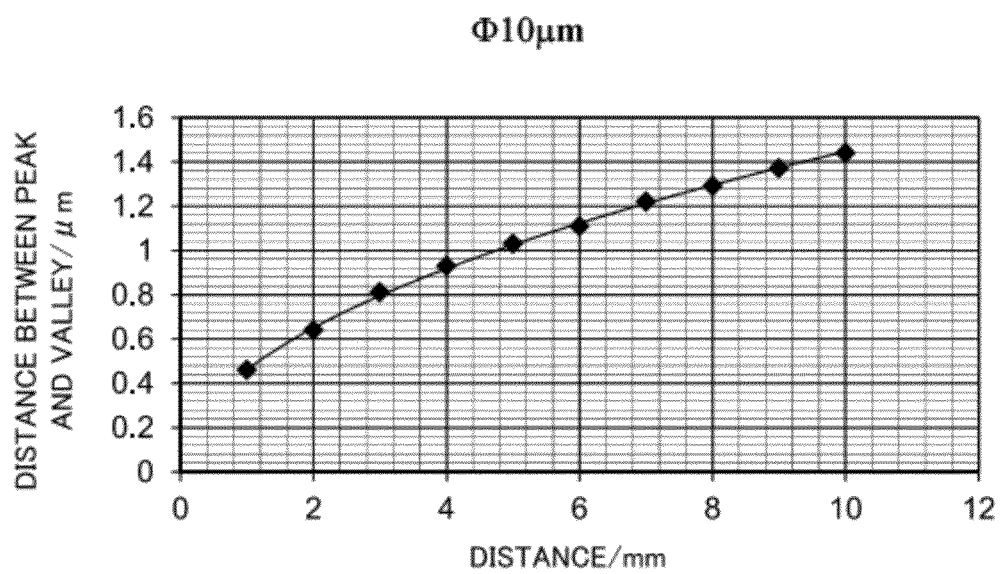
FIGS. 4 and 5 are graphs showing simulation results of a relationship between a distance f between a peak and a valley of intensity and a distance d between a specimen and a detector when a phase contrast is generated by plane wave in cases of specimen size of 10 μm and specimen size of 50 μm, respectively.
Figure 5:
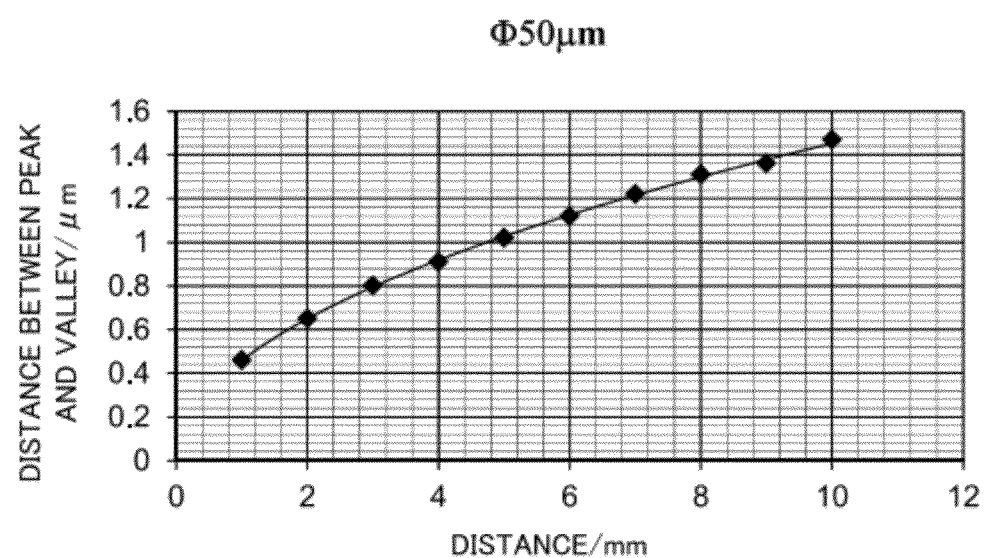
Figure 6:
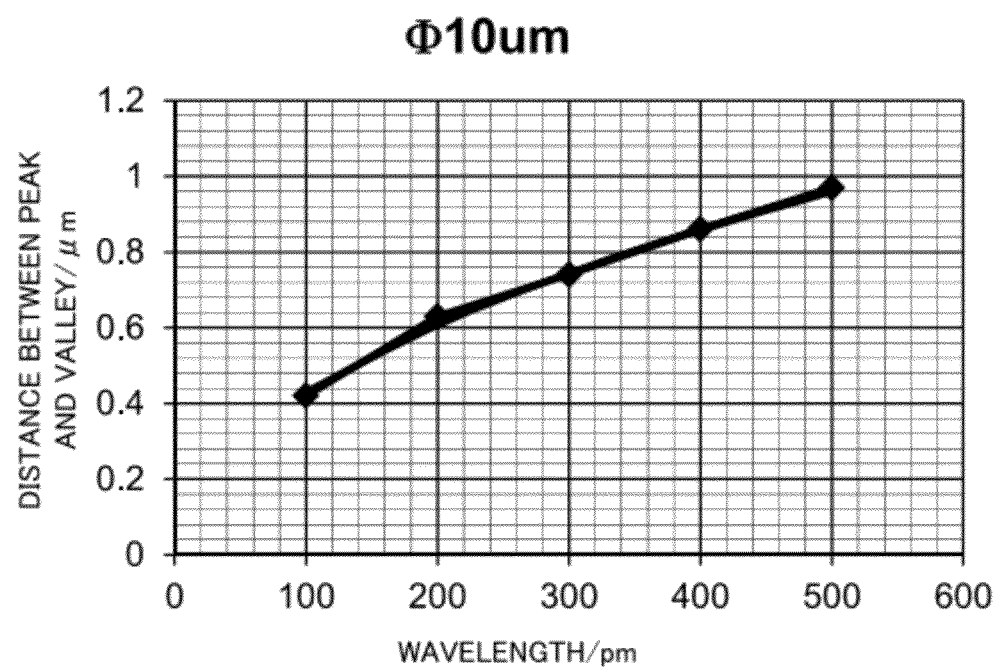
FIGS. 6 and 7 are graphs showing simulation results of a relationship between a distance between a peak and a valley of intensity and a wavelength λ of X-ray when a phase contrast is generated by plane wave in cases of specimen size of 10 μm and specimen size of 50 μm, respectively.
Figure 7:
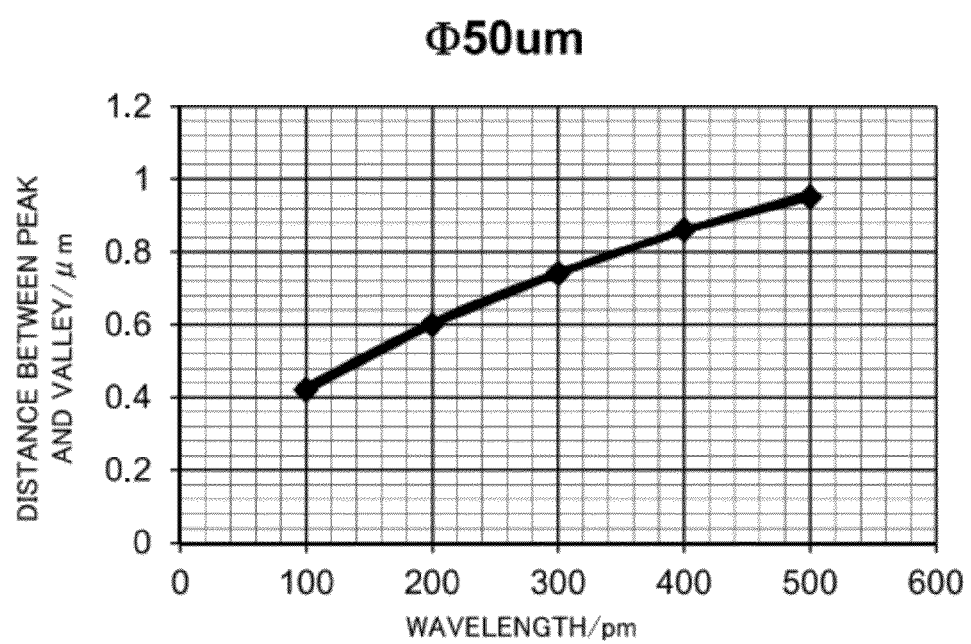

FIGS. 4 and 5 are graphs showing simulation results of a relationship between the distance f between the peak and the valley of intensity and the distance d between the specimen and the detector when a phase contrast is generated by plane wave with respect to cylindrical specimens having diameters of 10 μm and 50 μm, respectively. In this simulation, calculation is made with the wavelength $\lambda$ of the X-ray as 229 pm. As shown in FIGS. 4 and 5, the distance f becomes about 1 μm when d is 5 mm regardless of the diameter of the specimen. FIGS. 6 and 7 are graphs showing simulation results of a relationship between the distance f between the peak and the valley of intensity and the wavelength $\lambda$ of the X-ray when a phase contrast is generated by plane wave with respect to cylindrical specimens having diameters of 10 μm and 50 μm, respectively. In this simulation, the distance d from the specimen 500 to the detector 130 is 2 mm. As shown in FIGS. 6 and 7, the distance f becomes about 0.65 μm when the wavelength is, for example, 229 pm regardless of the diameter of the specimen. The above-mentioned formula (2) is the mathematization of the relationships.

Setting the f provided in such a manner to about the resolution of the detector 130 or more enables to emphasize the outline of a photographed image. However, an image with an edge emphasized in such a manner has a difference in intensity more than an actual difference in absorption coefficient, so that the image is not suitable for quantitative evaluation of absorption coefficient. For example, when an X-ray photographed image is used for CT reconstruction, the edge is emphasized too much when viewed in any direction, so that a strong artifact is generated and the reconstruction becomes difficult.

Therefore, the phase contrast is suppressed and an image by an absorption contrast is photographed for CT reconstruction. In this case, it is preferable to finely adjust the value of the phase contrast $f(\lambda, d)$ so as to be smaller than the value of the resolution $\Delta$ of the detector 130. Accordingly, in a case where an image is photographed by an absorption contrast, the phase contrast $f(\lambda, d)$ needs at least to satisfy the range of not less than ⅓ times and not more than 1 time of the resolution $\Delta$ of the detector 130. It is therefore required that the X-ray image photographing apparatus 100 is capable of fine adjustment of the arrangement of each unit at least within the range.

On the other hand, in a case where a transmission image is photographed with the edge emphasized, it is required to adjust the resolution $\Delta$ of the detector so as to be smaller than the value of the phase contrast $f(\lambda, d)$. Accordingly, both of an image of a phase contrast and an image of an absorption contrast can be photographed when observing a fine structure by adjusting the arrangement of each unit within the range that the phase contrast $f(\lambda, d)$ becomes not less than ⅓ times and not more than 3 times of the resolution $\Delta$ of the detector 130 as shown in the formula (1) upon photographing.

Experimental Example

Example 1

Figure 8:
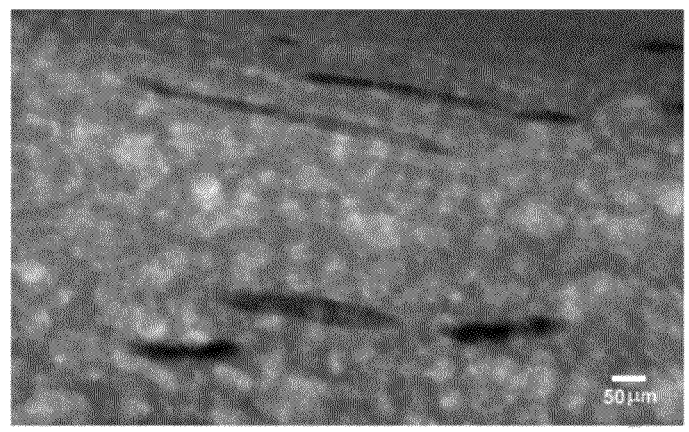
FIGS. 8 and 9 are X-ray transmission images of plant cells photographed when the distances between the specimen and the detector are set to 1 mm and 5 mm, respectively.
Figure 9:
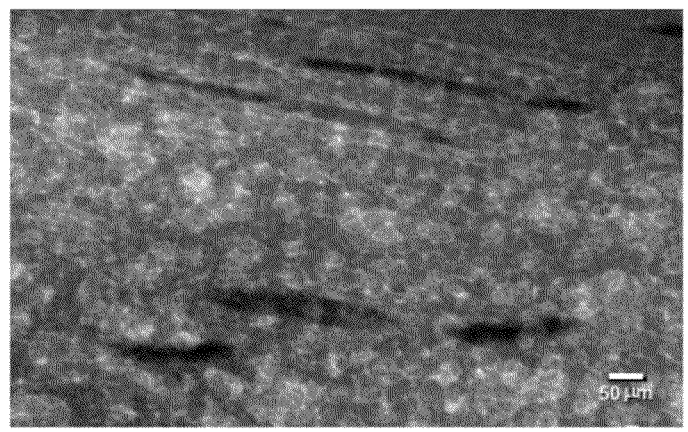

Next, an experiment using the X-ray image photographing apparatus 100 will be described. First, a leaf of a plant was used as the specimen and an X-ray transmission image using a phase contrast was photographed. The X-ray source 110 having a supply power of 875 W, Cr target, and a focal point size of 70 μm, and the detector 130 having a pixel size of 0.65 μm (space resolution of 0.65 μm) were used. The distance L between the X-ray source 110 and the specimen 500 was set to 250 mm. FIGS. 8 and 9 are X-ray transmission images of plant cells photographed when the distances d between the specimen 500 and the detector 130 are set to 1 mm and 5 mm, respectively.

As shown in FIG. 8, when the distance d is 1 mm, an X-ray transmission image by an absorption contrast in which edge of a cell wall is not emphasized was obtained. At the time, $f(\lambda, d)$ is 0.5 μm and smaller than 0.65 μm which is the resolution $\Delta$ of the detector. Furthermore, as shown in FIG. 9, when the distance d is set to 5 mm, an X-ray transmission image in which edge of a cell wall is emphasized was obtained. At the time, $f(\lambda, d)$ becomes 1.1 μm and larger than 0.65 μm which is the resolution $\Delta$ of the detector. In this manner, an image by a phase contrast whose outline is sharply defined can be obtained in a micron order by photographing an X-ray image under the arrangement where d/L is 0.1 which is sufficiently smaller than 1 and $f(\lambda, d)$ satisfies the above-mentioned formula (1).

Example 2

Under the same conditions as the above examples, an X-ray transmission image using an absorption contrast of a carbon fiber reinforced plastic (CRFP, carbon fiber reinforced resin) as a specimen was photographed, and three-dimensional CT reconstruction was performed. The distance L between the X-ray source 110 and the example 500 was set to 250 mm, and the distance d between the specimen 500 and the detector 130 was set 2 to 3 mm which is the middle of the above-mentioned two examples, and adjustment was performed for photographing so that phase contrast is not too emphasized.

Figure 10:
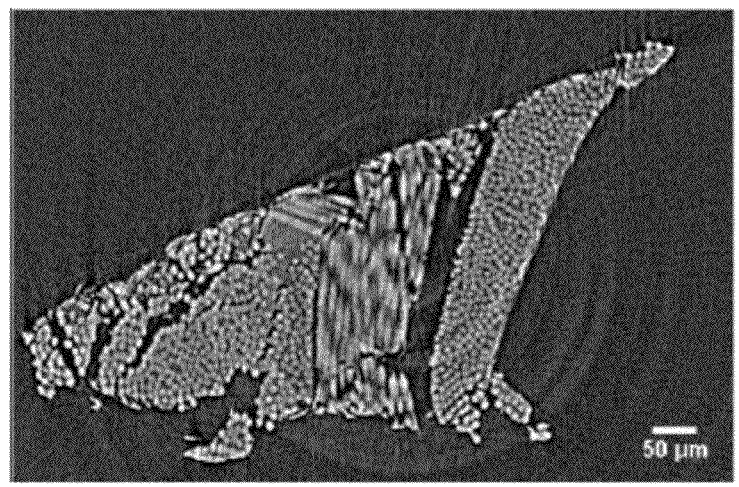
FIGS. 10, 11, and 12 are CT images of two orthogonal cross sections and an enlarged cross section of carbon fiber reinforced plastic (CFRP, carbon fiber reinforced resin), respectively.
Figure 11:
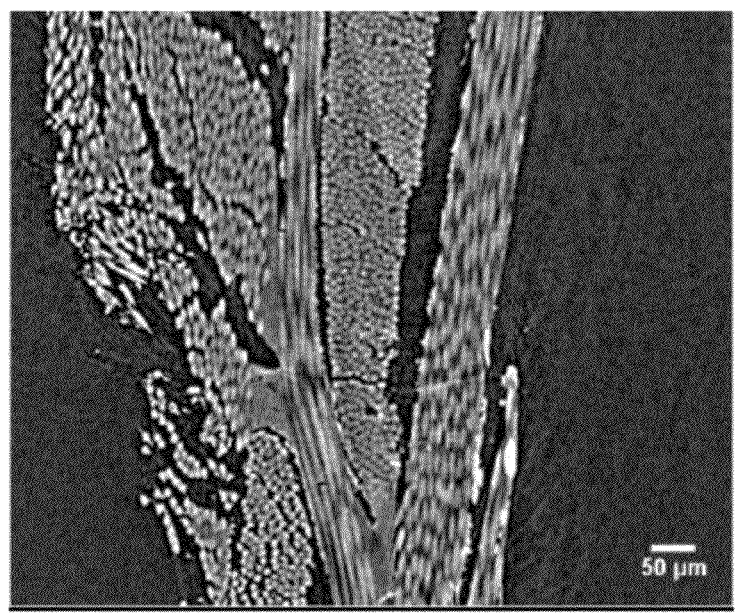
Figure 12:
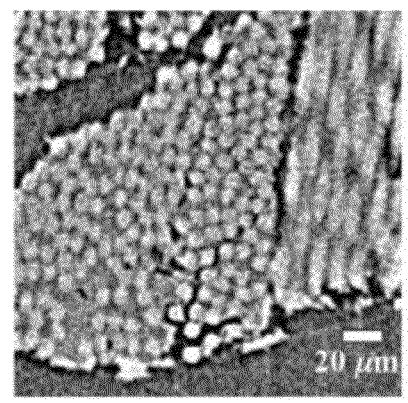

FIGS. 10, 11, and 12 are CT images of two orthogonal cross sections and an enlarged cross section of a carbon fiber reinforced plastic (CRFP, carbon fiber reinforced resin). Carbon fiber has a high strength in fiber direction although the strength is not enough in other directions. Accordingly, fibers whose fiver directions are different are overlapped in a multilayer. As shown in FIGS. 10 to 12, in the fiber, carbon fibers whose fiver orientations are changed to be overlapped, a plastic joining the carbon fibers, a void therebetween, etc., can be observed in a clearly distinguished manner. A large void of a crack state is generated by destruction of a joint at an interface.

Example 3

Figure 13:
FIGS. 13 and 14 are CT images of a cross section of a leg of an ant cut vertically and a cross section in the direction along the leg, respectively.
Figure 14:

Furthermore, under the same conditions as the above-mentioned embodiments, an X-ray transmission image using an absorption contrast of a joint portion of a leg of an ant as a specimen was photographed, and three-dimensional CT reconstruction was performed. The distance L between the X-ray source 110 and the specimen 500 was set to 250 mm, and the distance d between the specimen 500 and the detector 130 was adjusted to 2 to 3 mm for photographing. FIGS. 13 and 14 are CT images of a cross section of a leg of an ant vertically cut and a cross section in the direction along the leg. As shown in FIGS. 13 and 14, it was observed that there existed liquid and muscle tissue surrounded thereby at a portion inside an external skeleton of the leg. In this manner, an X-ray image was photographed under the condition that d/L was about 0.008 to 0.012 which is sufficiently smaller than 1, and a clear CT image of a micron order was obtained. As described above, it was verified to realize an X-ray microscope having a resolution of micron order.

Second Embodiment

Figure 15:
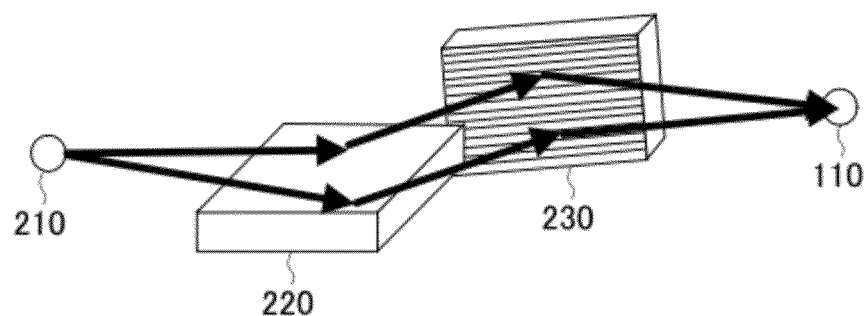
FIG. 15 is a diagram showing a configuration for generating a virtual source according to a second embodiment.

A minute focal point formed by focusing divergent X-ray by an X-ray optical element may be used as a virtual source for the X-ray source 110. FIG. 15 is a diagram showing a configuration for generating a virtual source as the X-ray source 110. As shown in FIG. 15, the configuration for generating the virtual source is configured of a real X-ray source 210 that radiates divergent X-ray, a first mirror 220, and a second mirror 230 (X-ray optical element), and as a result, the X-ray source 110 of a virtual source can be generated.

It is preferable that the size of the virtual source obtained in such a manner be 100 μm or less. It is more preferable that the size of the virtual source be 50 μm or less or 20 μm or less. When the size of the virtual source is from 10 μm to several tens μm, an effect of obtaining an X-ray image having resolution of about 1 μm becomes large. The virtual source may also be formed by using a pin hole or a slit to obtain a light source having an appropriate size.

As shown in FIG. 15, the first mirror 220 reflects the X-ray generated by the real X-ray source 210 in a plane parallel to the support table 120, and the second mirror 230 reflects the X-ray reflected by the first mirror 220 in a plane perpendicular to the support table 120.

For example, a multilayer mirror (multilayer optical element) may be used for the first mirror 220 and the second mirror 230. Herewith, only X-ray having a wavelength of characteristic line (CuKa) can be selectively taken out when focusing light by the first mirror 220 and focusing light by the second mirror 230. Furthermore, since a d-spacing can be changed by incident position of the X-ray, the d-spacing can be adjusted to cause diffraction even when the incident angle is changed.

The first mirror 220 and the second mirror 230 may be formed of a crystal plate (crystal optical element). Accordingly, for example, the first or second mirror is capable of taking out only X-ray of Kai. Furthermore, the first mirror 220 and the second mirror 230 may be formed of total reflection mirrors to limit the wavelength of reflected X-ray to long wavelength.

In this manner, by using a monochromatic virtual source obtained by a multilayer mirror or a crystal plate, photographing can be performed with a single λ. As a result, absorption coefficient can also be quantitatively calculated, CT reconstruction having quantitative density information becomes easy, and mapping of quantitative density also becomes possible. Furthermore, sufficient power for generating X-ray can be maintained while reducing the focal point size by using the virtual source.

What is claimed is:

1. An X-ray image photographing method that enables photographing of a fine structure with a high space resolution while using an X-ray source having a finite size, comprising:
   providing a detector having a resolution Δ;
   adjusting a distance d from the specimen to the detector, such that
   d/L is smaller than 1, when L is a distance from an X-ray source to a specimen and
   the following formula is satisfied:

$$\frac{\Delta}{3} \le 0.96\sqrt{\lambda \cdot d} \le 3\Delta$$

wherein λ is a wavelength component of monochromatic X-ray or a weighted average numerical number of plural wavelength components of monochromatic X-ray to be irradiated from the X-ray source.

2. The X-ray image photographing method according to claim 1 wherein,
   the d/L is 0.1 or less.

3. The X-ray image photographing method according to claim 1 wherein,
   a focal point size of the X-ray source is sufficiently larger than the Δ.

4. The X-ray image photographing method according to claim 1 wherein,
   the detector has a space resolution of 2 μm or less.

5. The X-ray image photographing method according to claim 1 wherein,
   a supply power when the X-ray source is used is 30 W or more.

6. The X-ray image photographing method according to claim 1 wherein,
   a fine focal point formed by monochromatizing and focusing divergent X-ray with an X-ray optical element is used as a virtual source for the X-ray source.

7. An X-ray image photographing apparatus comprising:
an X-ray source having a finite size and generating X-ray;
a support table supporting a specimen to which the generated X-ray is irradiated; and
a detector detecting X-ray transmitted through the specimen, wherein
d/L is set to be smaller than 1 and distance d is set to be in the range according to the following formula $$\frac{\Delta}{3} \leq 0.96\sqrt{\lambda \cdot d} \leq 3\Delta$$

by adjusting an arrangement of the X-ray source, the support table, and the detector to thereby enable photographing of a fine structure of the specimen,
wherein L is a distance from the X-ray source to the specimen, d is a distance from the specimen to the detector, $\lambda$ is a wavelength component of monochromatic X-ray or a weighted average numerical number of plural wavelength components of monochromatic X-ray to be irradiated from the X-ray source, and $\Delta$ is a resolution of the detector.

* * * * *